United States Patent
Spengler et al.

(10) Patent No.: US 10,598,651 B2
(45) Date of Patent: Mar. 24, 2020

(54) SENSING SYSTEM FOR DETECTING MACHINE FLUID DEGRADATION

(71) Applicant: Caterpillar Inc., Peoria, IL (US)

(72) Inventors: Philip C. Spengler, Washington, IL (US); Hind Abi-Akar, Peoria, IL (US); Jeffrey R. Ries, Metamora, IL (US)

(73) Assignee: Caterpillar Inc., Peoria, IL (US)

( * ) Notice: Subject to any disclaimer, the term of this patent is extended or adjusted under 35 U.S.C. 154(b) by 102 days.

(21) Appl. No.: 15/379,920

(22) Filed: Dec. 15, 2016

(65) Prior Publication Data
US 2018/0172661 A1   Jun. 21, 2018

(51) Int. Cl.
*G01N 33/28*   (2006.01)
*G01N 11/00*   (2006.01)
*G01N 21/3577*   (2014.01)
*G01N 21/64*   (2006.01)
*G01N 31/22*   (2006.01)

(52) U.S. Cl.
CPC ......... *G01N 33/2888* (2013.01); *G01N 11/00* (2013.01); *G01N 21/3577* (2013.01); *G01N 21/6428* (2013.01); *G01N 33/2882* (2013.01); *G01N 31/22* (2013.01); *G01N 2021/6439* (2013.01)

(58) Field of Classification Search
CPC .......... G01N 33/2888; G01N 21/3577; G01N 21/6428; G01N 11/00; G01N 33/2882
See application file for complete search history.

(56) References Cited

U.S. PATENT DOCUMENTS

| | | | |
|---|---|---|---|
| 4,997,772 A * | 3/1991 | Sutton | C08J 3/215 422/430 |
| 5,604,441 A | 2/1997 | Freese et al. | |
| 5,650,563 A * | 7/1997 | Cooper | G01M 3/228 73/40.7 |
| 7,219,536 B2 | 5/2007 | Liu et al. | |
| 7,391,225 B1 | 6/2008 | Lee et al. | |
| 7,900,507 B2 | 3/2011 | Kauffman | |
| 9,176,086 B2 | 11/2015 | Qi | |
| 2008/0143351 A1 | 6/2008 | Lee et al. | |
| 2009/0084171 A1 | 4/2009 | Kauffman | |
| 2010/0307745 A1* | 12/2010 | Lafitte | C09K 8/62 166/250.12 |

(Continued)

FOREIGN PATENT DOCUMENTS

DE   10331997 A1   11/2004
WO   9924812 A1   5/1999

OTHER PUBLICATIONS

Jim Fitch, Noria Corporation; "Determining Proper Oil and Filter Change Intervals: Can Onboard Automotive Sensors Help?"; article.

*Primary Examiner* — Samuel P Siefke
(74) *Attorney, Agent, or Firm* — Miller, Matthias & Hull

(57) ABSTRACT

A sensing system for sensing degradation of a machine fluid is disclosed. The sensing system may comprise a capsule including a dissolvable element. The dissolvable element may be configured to at least partially dissolve when placed in contact with the machine fluid having an acid content indicative of degradation of the machine fluid. The sensing system may further comprise a tracer encapsulated by the capsule. The tracer may be at least partially released from the capsule when the dissolvable element at least partially dissolves.

20 Claims, 12 Drawing Sheets

(56) References Cited

U.S. PATENT DOCUMENTS

| | | | |
|---|---|---|---|
| 2011/0076484 A1* | 3/2011 | Kawai | B01J 19/126 |
| | | | 428/328 |
| 2012/0040018 A1* | 2/2012 | Thierman | A61K 36/9068 |
| | | | 424/641 |
| 2015/0110867 A1* | 4/2015 | Floyd, III | A61N 5/06 |
| | | | 424/452 |
| 2015/0361840 A1 | 12/2015 | Cummins | |
| 2016/0184466 A1* | 6/2016 | Wagner | B29C 70/80 |
| | | | 424/1.29 |

\* cited by examiner

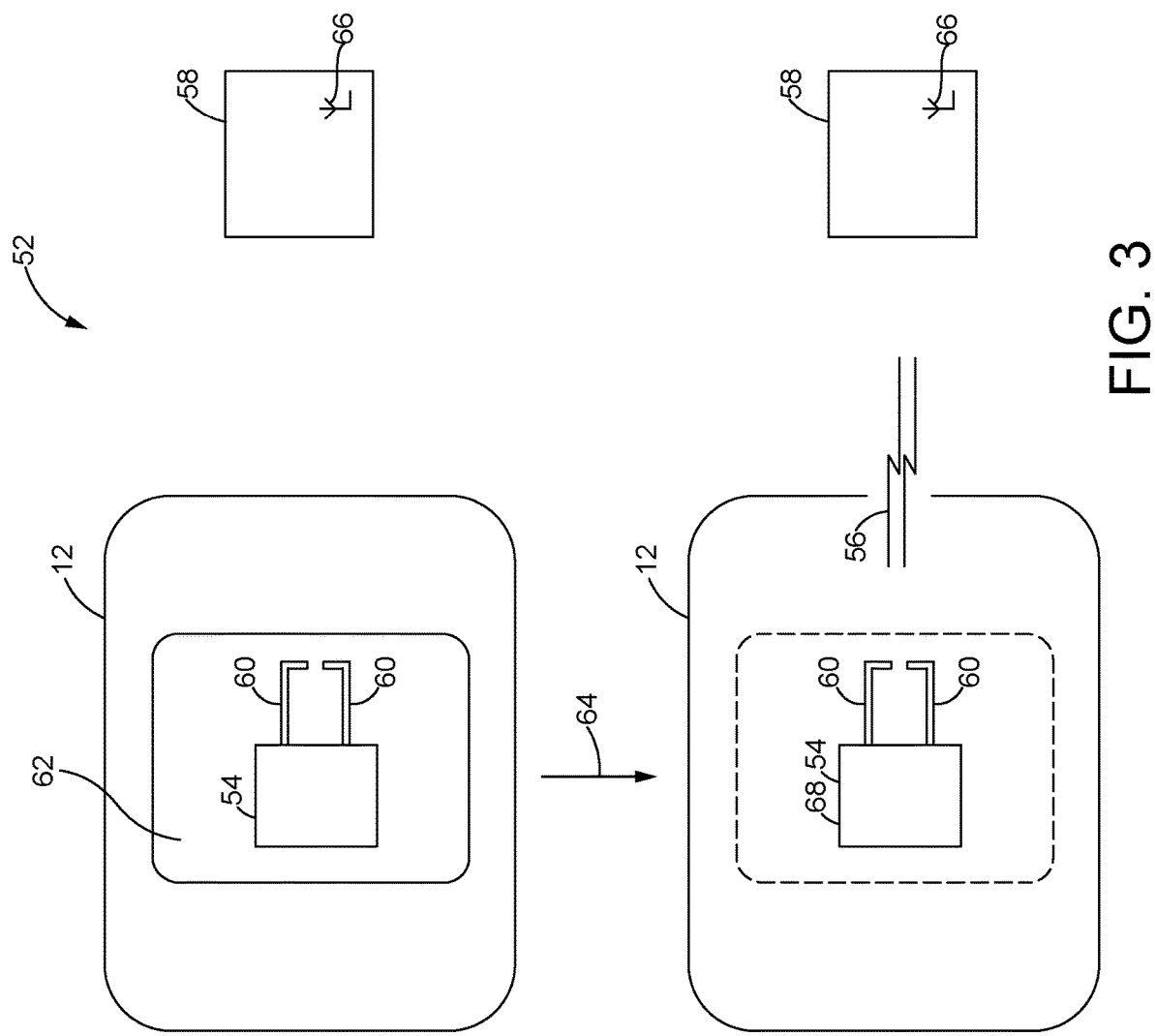

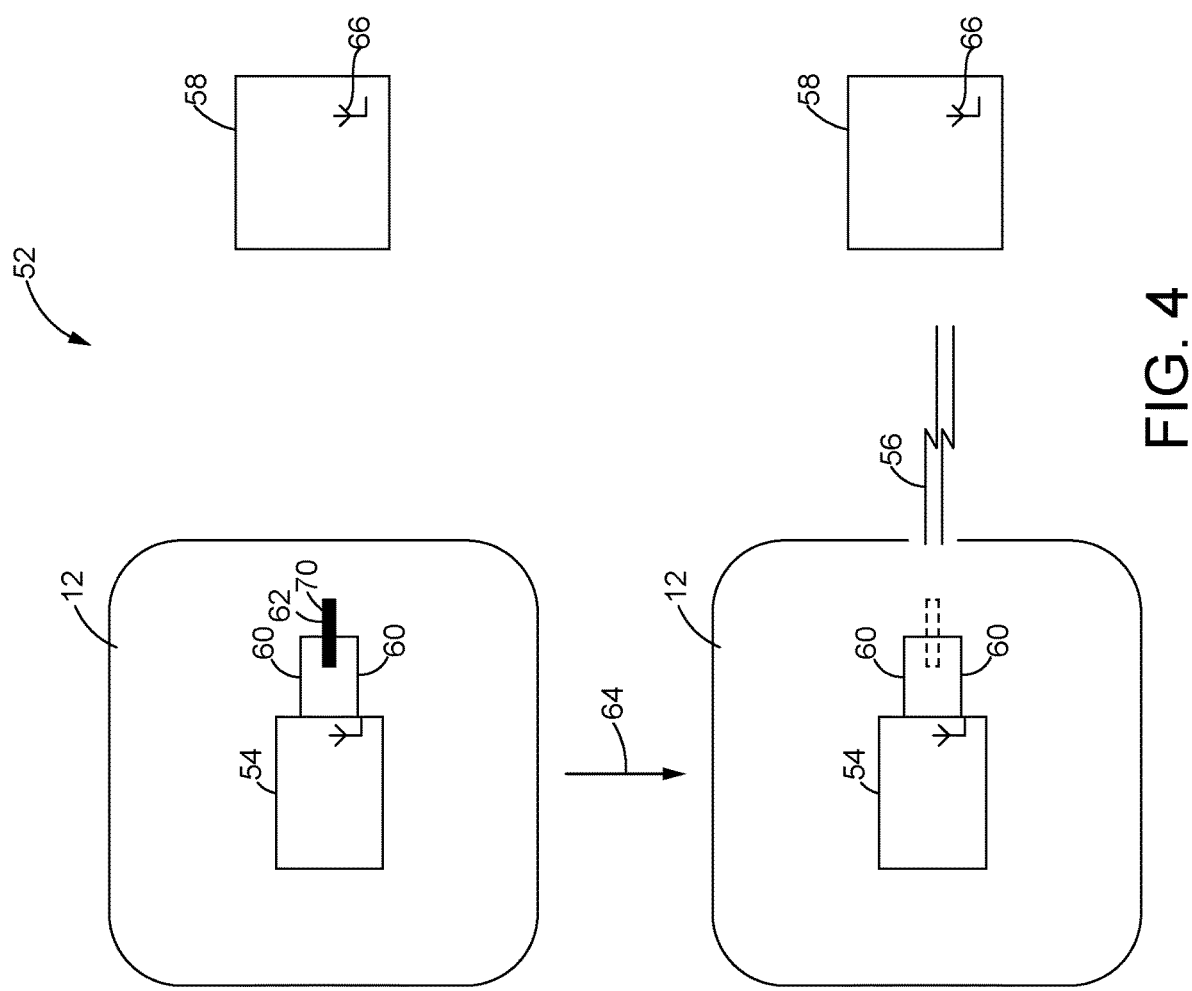

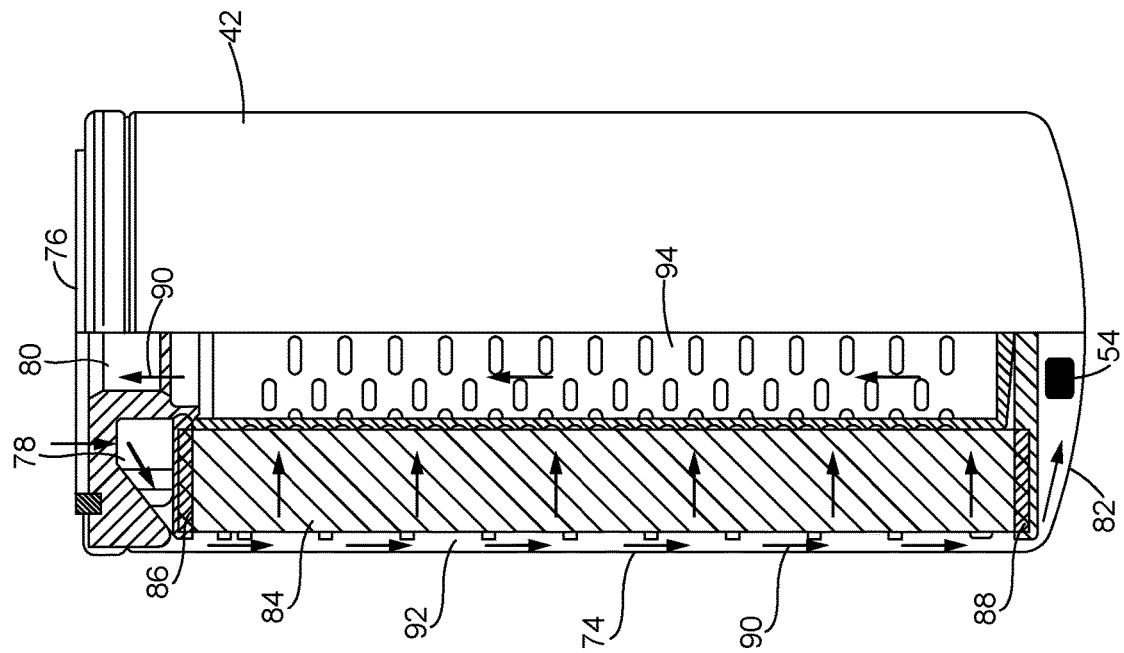
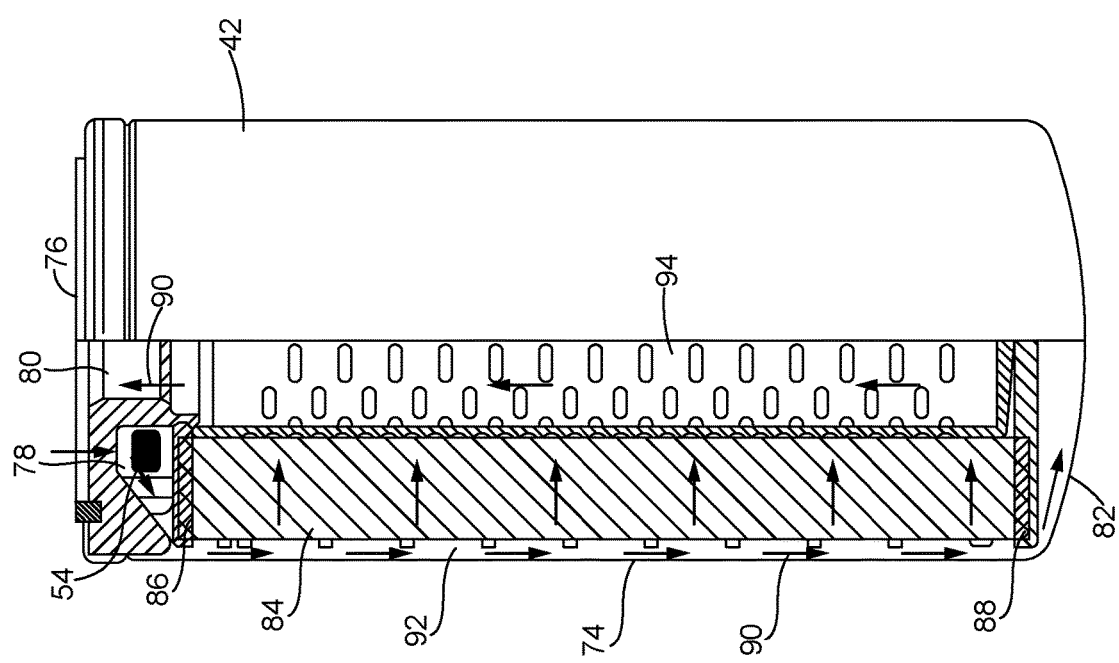

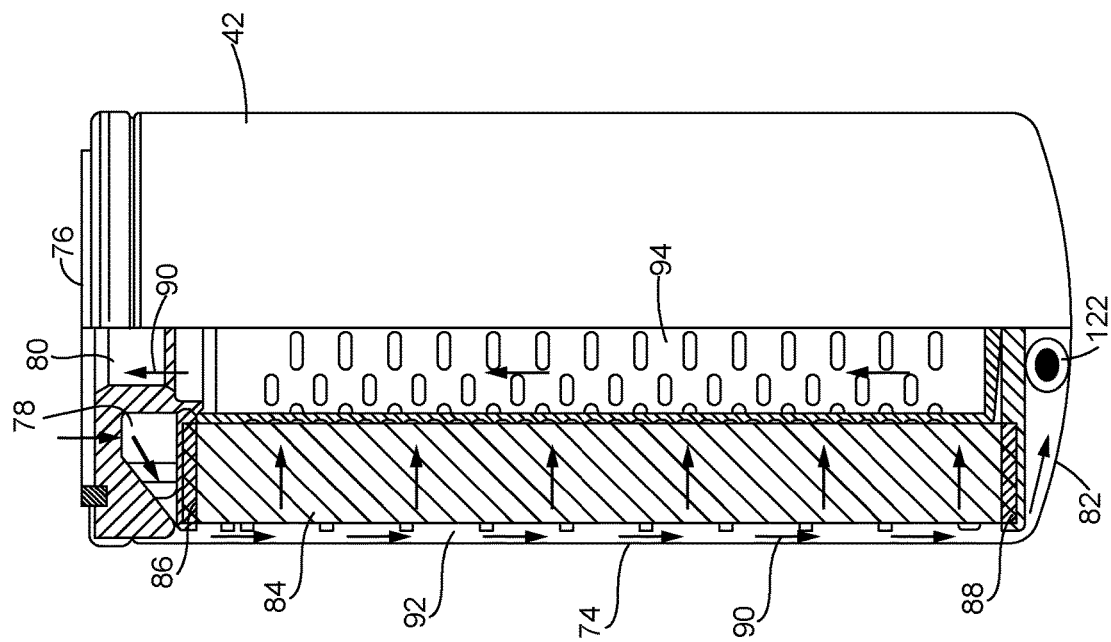
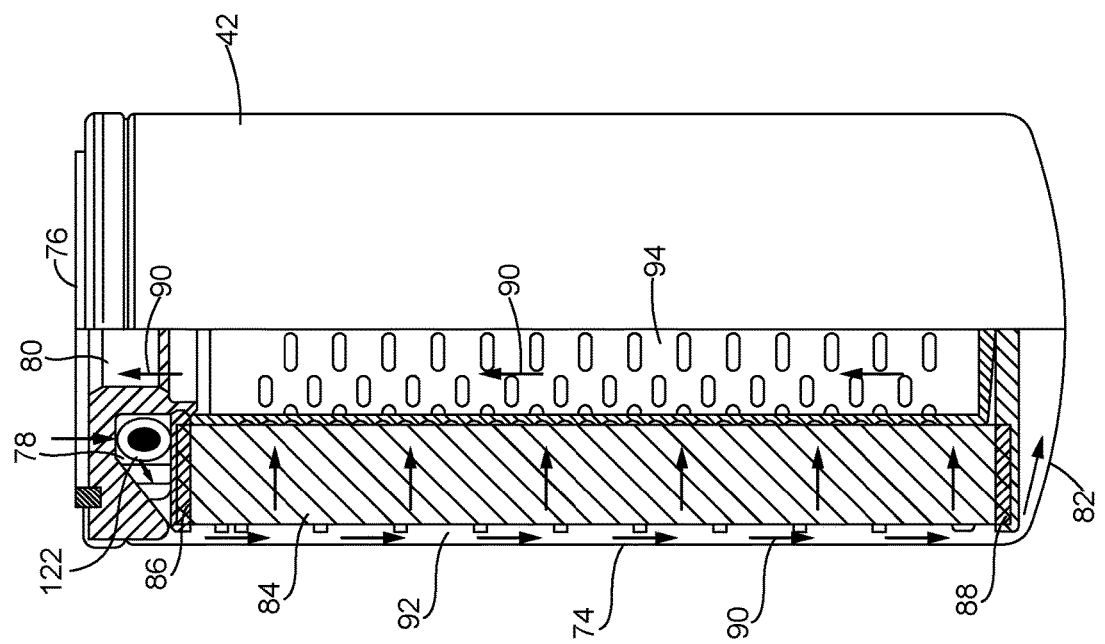

SENSING SYSTEM FOR DETECTING MACHINE FLUID DEGRADATION

TECHNICAL FIELD

The present disclosure generally relates to sensing systems and, more specifically, to sensing systems and methods for detecting the degradation of machine fluids such as engine oil, transmission fluid, hydraulic fluid, and coolant fluid.

BACKGROUND

Many machines and equipment circulate fluids that perform various functions such as lubricating moving parts, transferring heat, separating moving parts, absorbing contaminants, and powering hydraulic motors and hydraulic cylinders. Such fluids may include engine oil, transmission fluid, hydraulic fluid, and coolant fluid. For instance, engine oil and transmission fluid may lubricate moving parts such as gears and pistons, while hydraulic fluid may power hydraulic cylinders, such as those used to raise and lower an implement of an earth-moving machine. However, with extended hours of machine operation, such fluids may degrade due to oxidation, thermal breakdown, and/or contamination. For example, as an engine oil degrades, the acidity of the oil may increase, leading to an increase in the viscosity of the oil and eventual formation of sludge and varnish. When the acid content of the engine oil reaches a certain level, it may indicate that the engine oil has reached its useable life and needs to be replaced with fresh oil.

The machine or equipment may also include one or more filters that collect contaminants such as particles and debris that have accumulated in the fluids to protect bearing surfaces, engine liners, and/or other engine parts from wear. Although such filters may extend the period of service of the fluid, they may not be equipped to detect when the fluid has reached its useable life and needs to be replaced.

U.S. Pat. No. 7,043,402 discloses a sensing system for real-time monitoring of the quality of engine lubricating oil. The sensing system includes at least two electrodes installed on a port of a lubricating oil reservoir that monitor the quality of the lubricating oil based on impedance measurements. Other sensing systems for monitoring machine fluid quality may be complex and/or expensive to implement.

Thus, there is a need for improved sensing systems for detecting degradation of machine fluids.

SUMMARY

In accordance with one aspect of the present disclosure, a sensing system for sensing degradation of a machine fluid is disclosed. The sensing system may comprise a capsule including a dissolvable element. The dissolvable element may be configured to at least partially dissolve when placed in contact with the machine fluid having an acid content indicative of the degradation of the machine fluid. The sensing system may further comprise a tracer encapsulated by the capsule. The tracer may be at least partially released from the capsule when the dissolvable element at least partially dissolves.

In accordance with another aspect of the present disclosure, a filter for a machine fluid is disclosed. The filter may comprise a housing having an inlet and an outlet, a filter medium disposed in the housing, and a capsule disposed in the housing. The capsule may encapsulate a tracer, and may be formed from a dissolvable element. The dissolvable element may be configured to at least partially dissolve and at least partially release the tracer into the machine fluid when an acid content of the machine fluid reaches a level indicative of the degradation of the machine fluid. The release of the tracer into the machine fluid may signal the degradation of the machine fluid.

In accordance with another aspect of the present disclosure, a method for sensing degradation of a machine fluid is disclosed. The method may comprise placing a capsule in contact with the machine fluid, wherein the capsule encapsulates a tracer and is formed from a dissolvable element. The method may further comprise allowing the dissolvable element to at least partially dissolve and at least partially release the tracer into the machine fluid when an acid content of the machine fluid reaches a level indicative of the degradation of the machine fluid. The release of the tracer into the machine fluid may signal the degradation of the machine fluid.

These and other aspects and features of the present disclosure will be more readily understood when read in conjunction with the accompanying drawings.

BRIEF DESCRIPTION OF THE DRAWINGS

FIG. 3 is a schematic representation of a sensing system for detecting degradation of the machine fluid having a tag encapsulated in a dissolvable element, constructed in accordance with the present disclosure.

FIG. 4 is a schematic representation similar to FIG. 3, but with the dissolvable element positioned between electrical contacts of the tag, constructed in accordance with the present disclosure.

FIG. 5 is a partial cross-sectional view of a filter for the machine fluid having the tag disposed therein, constructed in accordance with the present disclosure.

FIG. 6 is a partial cross-sectional view similar to FIG. 5, but with the sensor placed at a different location in the filter, constructed in accordance with the present disclosure.

FIG. 12 is a partial cross-sectional view of the filter having the capsule disposed therein, constructed in accordance with the present disclosure.

FIG. 13 is a partial cross-sectional view similar to FIG. 12, but with the capsule placed at a different location in the filter, constructed in accordance with the present disclosure.

DETAILED DESCRIPTION

Figure 1:
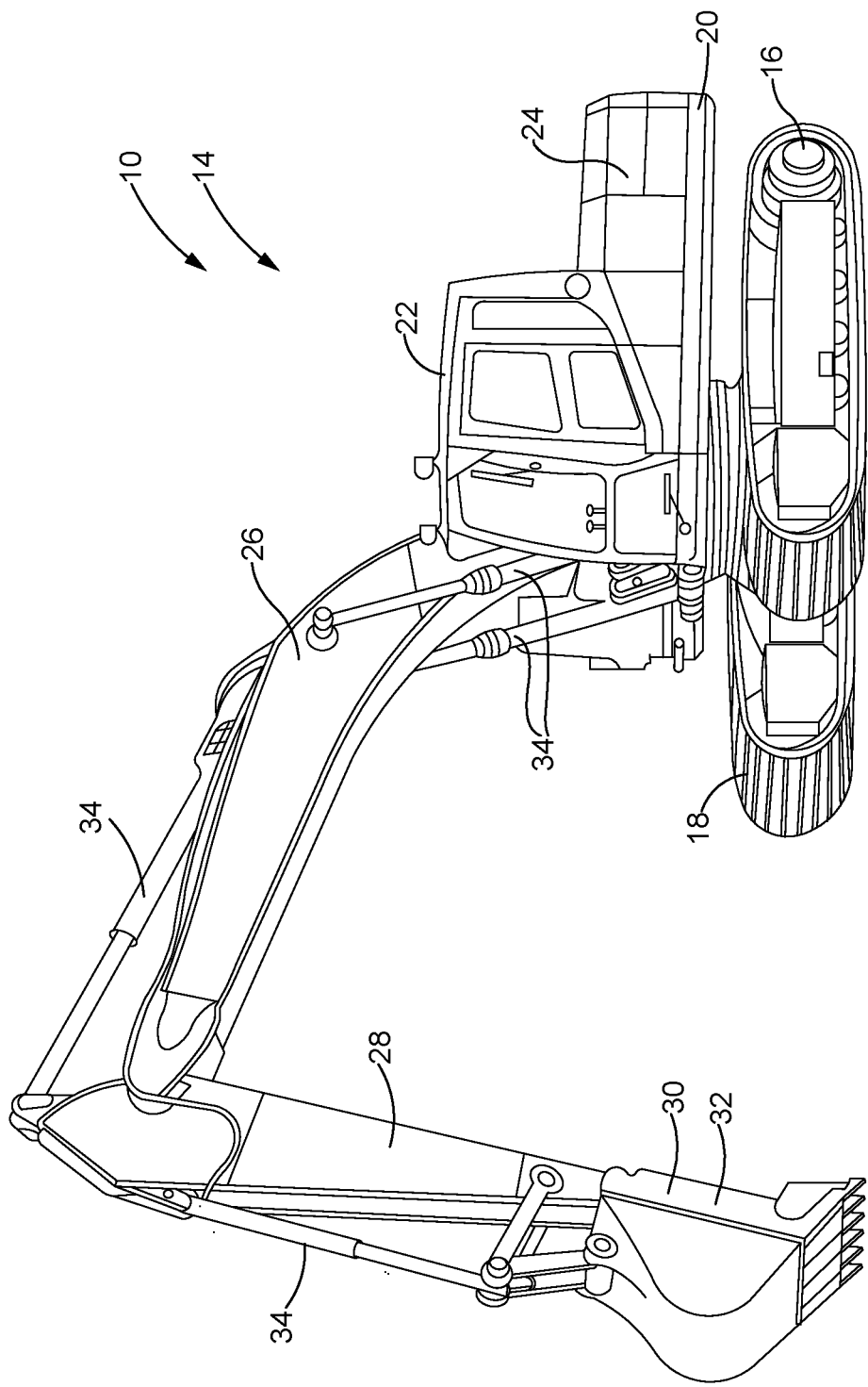
FIG. 1 is a side perspective view of a machine, constructed in accordance with the present disclosure.

Referring now to the drawings, and with specific reference to FIG. 1, a machine 10 is shown. The machine 10 may be any type of machine or equipment that circulates one or more machine fluids 12 (see FIG. 2) to perform one or more functions such as, but not limited to, lubricating moving parts or separating moving parts of the machine, actuating hydraulic cylinders, powering hydraulic motors, transferring heat, and absorbing contaminants. In this regard, a "machine fluid" as used herein may include various types of machine fluids apparent to those with ordinary skill in the art such as, but not limited to, engine oil, transmission fluid, hydraulic fluid, coolant fluid, or fuel.

As a non-limiting example, the machine 10 may be an earth-moving machine such as an excavator 14. In this example, the machine 10 may include an undercarriage 16 supporting tracks 18 (or wheels) to drive the movement of the machine 10, and a rotatable platform 20 configured for rotation with respect to the undercarriage 16. The rotatable platform 20 may support an operator cab 22, an internal combustion engine 24, and a boom 26 pivotally mounted on the rotatable platform 20. An arm 28 may be pivotally carried by the boom 26, and the arm 28 may pivotally carry an implement 30, such as a bucket 32. Adjustment of the position of the boom 26, the arm 28, and the implement 30 may be accomplished using hydraulic cylinders 34 actuated with pressurized hydraulic fluid, as will be understood by those with ordinary skill in the art. In alternative arrangements, the machine 10 may be various other types of machines such as, but not limited to, earth-moving machines or equipment, drilling machines or equipment, mining machines or equipment, automotive vehicles, and marine vehicles.

Figure 2:
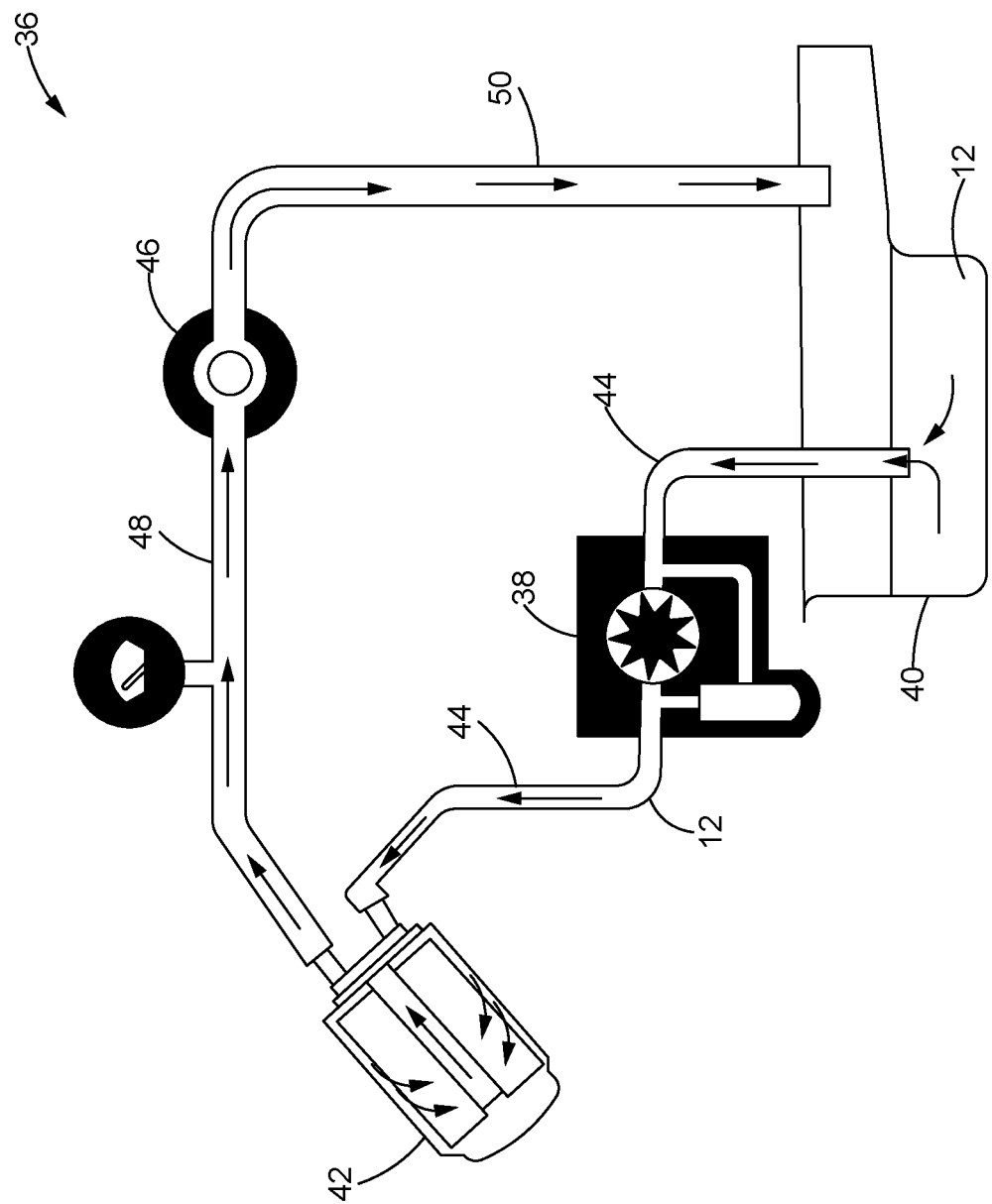
FIG. 2 is a schematic representation of a fluid circuit of a machine fluid used by the machine of FIG. 1, constructed in accordance with the present disclosure.

Turning now to FIG. 2, a fluid circuit 36 generally depicting a flow path of the machine fluid 12 though the machine 10 is shown. A pump 38 may actively drive the flow of the fluid 12 through the circuit 36. The pump 38 may draw the fluid 12 from a fluid reservoir 40 (e.g., a sump, etc.) and may drive the flow of the fluid 12 through a filter 42 via one or more conduits 44. The filter 42 may remove contaminants and particulates in the fluid 12 before the fluid 12 is directed to one or more targets 46 through one or more conduits 48. It will be understood that the target(s) 46 may vary considerably depending on the type of the machine fluid used. For instance, if the machine fluid 12 is engine oil or transmission fluid, the targets 46 may include moving parts of the machine 10 such as the transmission gears or the engine pistons for lubrication thereof. Alternatively, if the machine fluid 12 is hydraulic fluid, the targets 46 may include hydraulic motors and/or the hydraulic cylinders 34 that adjust the position of the implement 30 (or the boom 26, the arm 28, etc.) of the machine 10. After reaching the target(s) 46, the machine fluid 12 may be cycled back to the reservoir 40 through one or more conduits 50, allowing the process to repeat. Those with ordinary skill in the art will understand that the flow circuit 36 of FIG. 2 may be considerably more complex in practice and may include additional components such as valves, additional pumps, and/or pressure gauges, among other components. In other arrangements, the pump 38 may be downstream of the filter 42, or the flow of the fluid 12 through the circuit 36 may occur passively without the use of a pump.

Referring to FIG. 3, a sensing system 52 for detecting the degradation of the machine fluid 12 is shown. Degradation of the machine fluid 12 may occur when the quality of the machine fluid 12 has decreased to a level that requires the replacement of the machine fluid 12 with fresh fluid. More specifically, the degradation of the machine fluid 12 may occur when the acid content of the machine fluid 12 increases to a level characteristic of degradation of the fluid. Thus, it will be understood that the acid content at which degradation of the machine fluid 12 occurs may vary considerably depending on the type of the machine fluid 12 used, as well as varying standards characterizing the degradation of the machine fluid.

The sensing system 52 may include a tag 54 that is configured to transmit a signal 56 to a remote reader 58 when the acid content of the machine fluid 12 reaches a level indicative of degradation of the machine fluid 12. The signal 56 may be a wireless signal, such as a wireless radio-frequency (RF) signal. For instance, the tag 54 may be a radio-frequency (RF) tag. The tag 54 may include two or more electrical contacts 60 that come into electrical communication and permit transmission of the signal 56 to the remote reader 58 when the machine fluid 12 degrades. The tag 54 may be surrounded or encapsulated by a dissolvable element 62 that separates the electrical contacts 60 and obstructs electrical communication between the contacts 60 prior to degradation of the fluid 12.

As shown in FIG. 3, the tag 54 encapsulated in the dissolvable element 62 may be placed in contact with the machine fluid 12 during use. As the machine fluid 12 ages and begins to degrade 64, the acid content in the machine fluid 12 may increase. The increased acidity of the machine fluid 12 may cause the dissolvable element 62 to at least partially dissolve, allowing the machine fluid 12 to flow between the electrical contacts 60 and permit electrical communication between the contacts 60. When in electrical communication, the electrical contacts 60 may complete the circuit of the tag 54, enabling the transmission of the signal 56 to the remote reader 58. An antenna 66 of the remote reader 58 may capture the signal 56 transmitted by the tag 54, thereby providing a positive indicator of machine fluid degradation at the remote reader 58.

The remote reader 58 may be associated with a hand-held device that enables an operator or technician to monitor the degradation of the machine fluid 12 remotely. In other arrangements, the remote reader 58 may be associated with or may communicate with a remote operator interface such as a computer or internet-enabled device to allow an operator or technician to track the quality of the machine fluid 12 from a remote work station. As yet another alternative, the remote reader 58 may be associated with or may communicate with an operator interface of the machine 10, such as a computer or display in the operator cab 22. In any event, receipt of the signal 56 at the remote reader 58 may inform the operator or technician that the machine fluid 12 has degraded and needs to be replaced with fresh fluid.

The tag 54 may be a chip 68 configured to transmit the wireless signal 56 when the contacts 60 are in electrical communication. For example, the tag 54 may be a radio-frequency identification (RFID) chip that transmits an RF signal in a frequency range compliant with RFID. For instance, the signal 56 may have a frequency in the range of about 860 to about 915 megahertz (MHz), although the frequency range may vary depending on varying standards characterizing RFID signals. In addition, the RFID chip may be passive and may be powered by the remote reader 58. In this case, the RFID chip may collect energy from the remote reader 58 and may transmit the signal 56 to the remote reader 58 when the electrical contacts 60 are in electrical communications. However, the RFID chip may also be active and may include a local power source, such as a battery.

Alternatively, the signal 56 transmitted by the tag 54 may be in a frequency range characteristic of BLUETOOTH® signals. That is, the signal 56 may have a frequency ranging from about 2.4 gigahertz (GHz) to about 2.485 GHz, but may also deviate from this range depending on varying standards characterizing BLUETOOTH® signals. Accordingly, in this arrangement, the chip 68 may be a BLUETOOTH® chip.

As yet another possibility, the signal 56 transmitted by the tag 54 may be in a frequency range characteristic of wireless fidelity (WI-FI®) signals. That is, the signal 56 may have a frequency of about 2.4 GHz, about 3.6 GHz, about 4.9 GHz, about 5 GHz, or about 5.9 GHz, but may also deviate from these frequencies depending on varying standards characterizing WI-FI® signals. In this arrangement, the chip 68 may be a WI-FI® chip.

The dissolvable element 62 may be formed from one or more compounds that is sensitive to acid and at least partially dissolves in the machine fluid 12 under acidic conditions. The chemical identity of the dissolvable element 62 may be chosen such that the dissolvable element 62 at least partially dissolves at the acid content that is characteristic of degradation of the particular machine fluid 12 used. As an illustrative example, if degradation of the machine fluid 12 is indicated at a total base number of 4, as measured by standard tests ASTM D2896, D4793 and/or equivalent tests, the chemical identity of the dissolvable element 62 may be chosen such that the dissolvable element 62 at least partially dissolves when the total base number of the machine fluid 12 reaches 4. Those with ordinary skill in the art will understand that the acid content at which the dissolvable element 62 at least partially dissolves will depend on the type of machine fluid 12 used, its acid tolerance, as well as established acid tolerance limits of the particular machine fluid. As non-limiting possibilities, the dissolvable element 62 may be formed from or may include a compound such as magnesium oxide (MgO), zinc oxide (ZnO), cadmium oxide (CdO), and combinations thereof. Other types of suitable metal oxides, or combinations thereof, may also be used.

The electrical contacts 60 may be formed from a conductive material that is chemically stable in the machine fluid 12. For example, the electrical contacts 60 may be formed from a ferrous material, such as iron or an iron alloy. In other arrangements, the electrical contacts 60 may be formed from other types of metals, metal alloys, or other conductive materials that are chemically stable in the machine fluid 12.

Turning to FIG. 4, an alternative design of the sensing system 52 is shown. In this arrangement, the dissolvable element 62 may be a disk-shaped structure 70 positioned between and separating the electrical contacts 60 to obstruct electrical communication therebetween. Although shown as rectangular, the disk-shaped structure 70 may have any shape insertable between the electrical contacts 60 such as, but not limited to, circular, polygonal, or amorphous shapes.

As the machine fluid 12 begins to degrade 64 and the acid content of the fluid increases, the dissolvable element 62 may at least partially dissolve, allowing the contacts 60 to come into physical contact to permit electrical communication therebetween. In some arrangements, the contacts 60 may be spring-loaded to drive the contacts 60 into physical contact upon dissolution of the dissolvable element 62, as will be understood by those with ordinary skill in the art. Alternatively, the electrical contacts 60 may remain separated upon dissolution of the dissolvable element 62, and the machine fluid 12 may flow between the contacts 60 to complete the circuit and allow electrical communication between the contacts 60. In any of the above arrangements, electrical communication between the contacts 60 may allow the tag 54 to transmit the signal 56 to the remote reader 58, indicating that the machine fluid 12 has degraded.

As shown in FIG. 5, the tag 54 may be placed in the filter 42 for the machine fluid 12. In some instances, the tag 54 may be secured to a particular location in the filter 42. As one possibility, the filter 42 may be a spin-on filter including a housing 74 having a top end 76 defining an inlet 78 and an outlet 80 for the machine fluid 12, a bottom end 82, and a filter medium 84 disposed in the housing 74 for trapping particulates and contaminants in the machine fluid 12. The filter medium 84 may be disposed between a top end cap 86 near the top end 76, and a bottom end cap 88 near the bottom end 82. The machine fluid 12 may follow a flow path 90 through the filter 42, as shown in FIG. 5. Specifically, the fluid 12 may enter the filter 42 through the inlet 78 at the top end 76 and subsequently flow along an outer periphery 92 of the filter 42 and through the filter medium 84 into a center tube 94 before exiting through the outlet 80 at the top end 76. Some of the fluid 12 may reach the bottom end 82 before flowing up flowing up through the center tube 94, as shown.

The tag 54 may be placed on the "dirty side" of the filter 42. That is, the tag 54 may be placed on the side of the filter 42 containing the fluid 12 that has not been completely filtered through the filter medium 84. For instance, as shown in FIG. 5, the tag 54 may be placed inside the housing 74 near the inlet 78 between the top end 76 and the top end cap 86. Alternatively, as shown in FIG. 6, the tag 54 may be placed inside the housing 74 between the bottom end 82 and the bottom end cap 88. In other arrangements, the tag 54 may be placed along the outer periphery 92 of the filter 42, or on the "clean side" of the filter 42 such as in the center tube 94 or near the outlet 80. In any event, as the acid content of the machine fluid 12 flowing through the filter 42 increases to a level indicative of degradation, the tag 54 may transmit the signal 56 to the remote reader 58 to signal degradation as described above.

It will be understood that the structure of the filter 42 of FIGS. 5-6 is merely exemplary and that the filter 42 may be any type of engine oil filter, transmission fluid filter, hydraulic fluid filter, coolant filter, or fuel filter apparent to those with ordinary skill in the art. In such arrangements, the tag 54 may be placed on the dirty side or on the clean side of the filter at various locations. Variations such as these also fall within the scope of the present disclosure.

Figure 7:
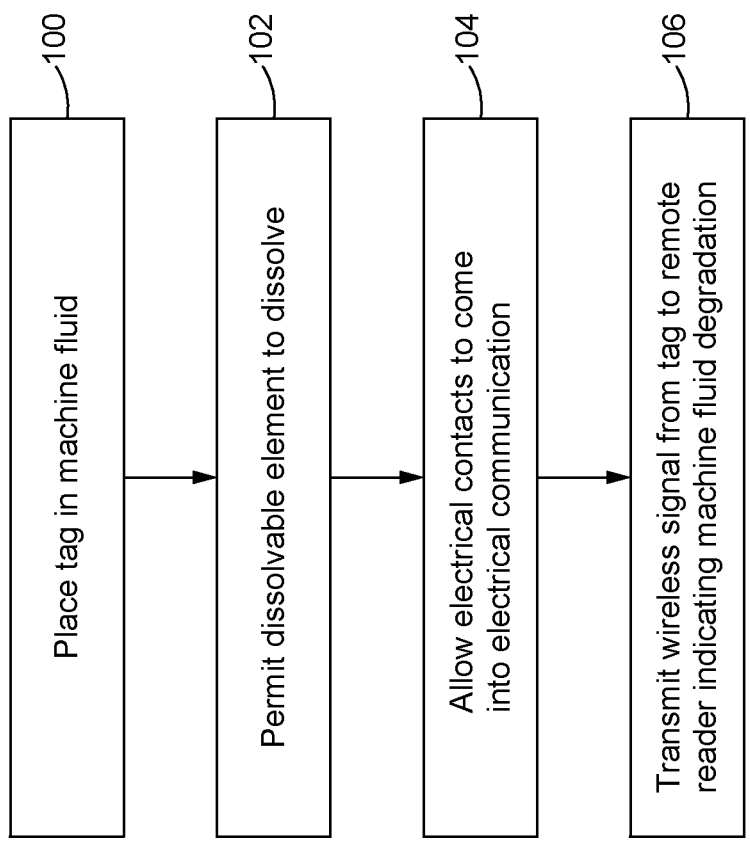
FIG. 7 is a flowchart of a series of steps involved in detecting the degradation of the machine fluid using the sensing system of FIGS. 3-6, in accordance with a method of the present disclosure.

Referring to FIG. 7, a series of steps that may be involved in detecting degradation of the machine fluid 12 using the sensing system 52 is shown. Beginning with a first block 100, the tag 54 may be placed in contact with the machine fluid 12. For example, the tag 54 may be a pill-like structure that is placed inside of the filter 42 (see FIGS. 5-6), or at another location in the fluid circuit 36. At a next block 102, the dissolvable element 62 may be permitted to at least partially dissolve when the acid content of the machine fluid 12 increases as a result of degradation. Dissolution of the dissolvable element 62 may then allow the electrical contacts 60 that were previously separated by the dissolvable element 62 to come into electrical communication (block 104). Once the electrical contacts 60 are in electrical communication, the circuit of the tag 54 may be completed, thereby permitting the tag 54 to transmit the signal 56 to the remote reader 58 indicating degradation of the machine fluid 12 (block 106).

Figure 8:
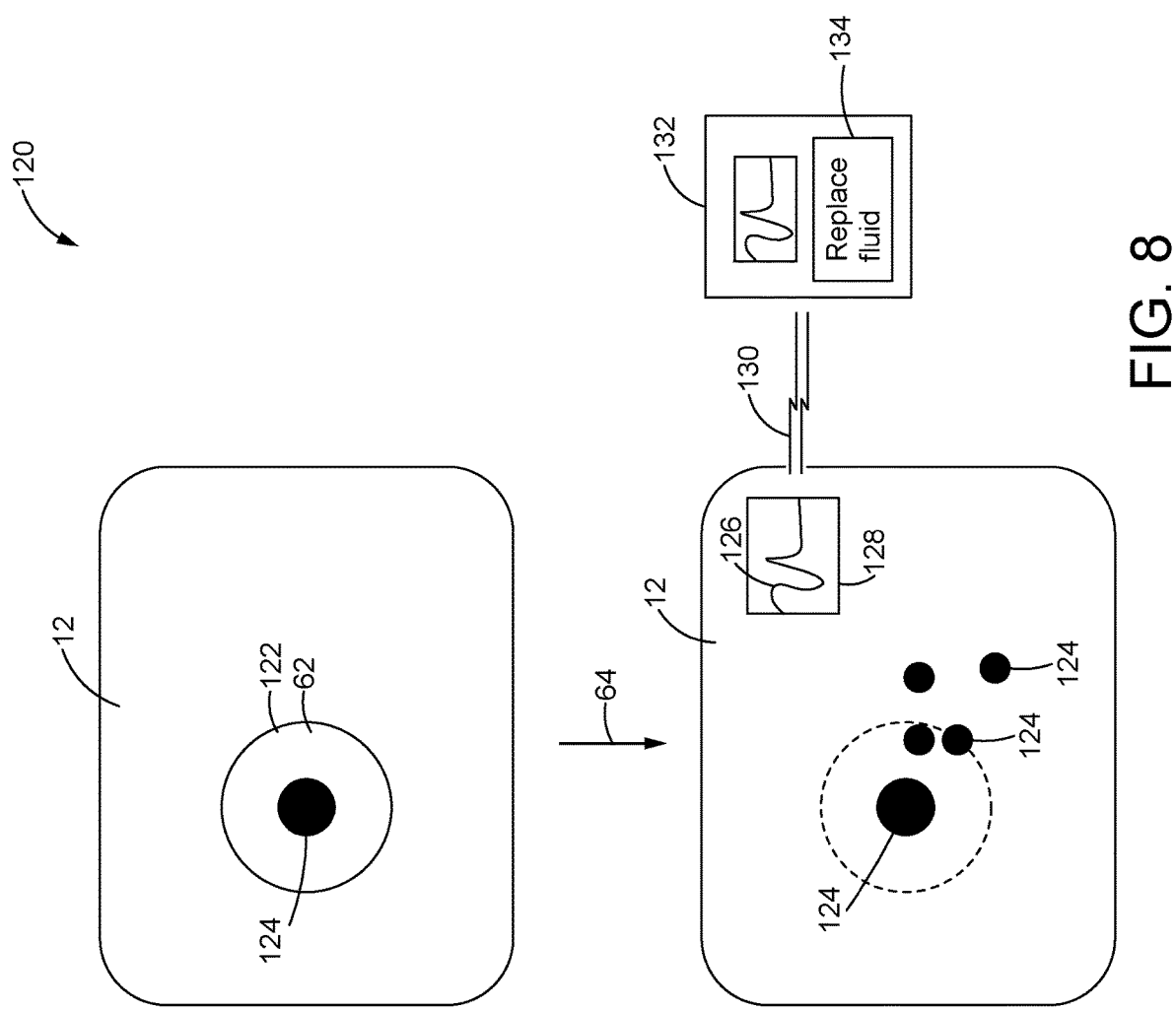
FIG. 8 is a schematic representation of another sensing system for detecting degradation of the machine fluid including a capsule encapsulating a tracer, constructed in accordance with the present disclosure.

Another sensing system 120 for sensing the degradation of the machine fluid 12 is schematically depicted in FIG. 8. The sensing system 120 may include a capsule 122 that is partially or entirely formed from the dissolvable element 62. The capsule 122 may be a pill-like structure that is placed in contact with or immersed in the machine fluid 12 to detect degradation of the machine fluid 12. The capsule 122 may surround or encapsulate a tracer 124. Although shown as circular, the capsule 122 may have any shape such as, but not limited to, oval, rectangular, polygonal, or amorphous shapes.

As the acid content of the machine fluid 12 reaches a level indicative of degradation 64, the dissolvable element 62 may dissolve, creating openings or pores in the capsule 122 that allow the release of the tracer 124 into the surrounding machine fluid 12. The release of the tracer 124 into the machine fluid 12 may signal the degradation of the machine fluid 12, indicating that the machine fluid 12 should be replaced with fresh fluid.

The tracer 124 may be a fluid (liquid or gas), a solid, or combinations thereof. The tracer 124 may include or may be formed from one or more compounds or elements that produce one or more characteristic signals 126 when released into the machine fluid 12. As non-limiting examples, the characteristic signal 126 of the tracer 124 may be an optical, spectroscopic, radioactive, magnetic, or electrical signal such as, but not limited to, a visible color change, ultraviolet (UV)/visible absorption signals, fluorescence emission signals, infrared (IR) absorption signals, and/or current or voltage signals. For instance, the tracer 124 may include one or more dyes having chromophores that absorb UV or visible light at characteristic wavelengths, and/or that color stain the machine fluid 12 to allow naked eye detection. In other arrangements, the tracer 124 may include one or more fluorescent or phosphorescent compounds or elements that emit fluorescent or phosphorescent signals at characteristic wavelengths. Examples of suitable dyes and fluorescent compounds may include, but are not limited to, transition metal salts (e.g., copper sulfate), transition metal complexes, cyanine dyes, boron-dipyrromethene (BODIPY) dyes, azo dyes, rhodamine dyes, fluorescein dyes, coumarin dyes, anthracene compounds, Alexa Fluor® dyes, as well as various organic or organometallic photoluminescent materials and polymers.

Alternatively or in combination with this, the tracer 124 may include a compound or element having infrared (IR)-active vibrational modes to permit detection by IR detection methods. For example, the tracer 124 may be a metal, a metal salt, a metal complex, an organometallic complex, a polymer, or an organic compound with characteristic absorption bands in the IR region. Alternatively or in combination with any of the above, the tracer 124 may undergo chemical transformation, energy transfer, or binding events with other molecules when released into the machine fluid 12 to produce the characteristic signal 126, or to generate a detectable product or complex. In other examples, the tracer 124 may alter the viscosity of the machine fluid 12 to allow detection of the release of the tracer 124 by viscosity or rheology measurements. As explained in further detail below, the presence of the tracer 124 in the machine fluid 12 may also be detected using chemical identification techniques (e.g., liquid chromatography, gas chromatography, FT-IR spectroscopy, nuclear magnetic resonance (NMR) spectroscopy, mass spectrometry, etc.). The use of chemical identification techniques may be beneficial, for example, if the tracer 124 (or a product or complex formed thereby) does not produce a clearly-identifiable visible, spectroscopic, or electrical signal.

In some arrangements, the sensing system 120 may include an on-machine detector 128, such as an instrument or a sensor chip, to detect the release of the tracer 124 into the machine fluid 12. For example, the detector 128 may be placed at one or more locations of the fluid circuit 36 such as in the reservoir 40, in the filter 42, or in the conduits 44, 48, and 50, so that the detector 128 is exposed to the machine fluid 12 flowing through the circuit 36. Alternatively, additional flow paths may be introduced into the fluid circuit 36 to transport quantities of the machine fluid 12 to the detector 128. Depending on the type of tracer 124 used, the detector 128 may be various types of detectors such as, but not limited to, a single or variable wavelength UV/vis detector (e.g., a diode array detector, a photodiode array detector, etc.), a fluorescence detector, a light scattering detector, a viscometer or rheometer, an IR detector, or a current or voltage detector. The detector 128 may transmit electronic or wireless signals 130 containing raw or processed data to a reader 132. The reader 132 may collect the raw or processed data for display at a hand-held device, a remote work station, or an operator interface (e.g., a computer display) of the machine 10, allowing the operator or technician to monitor the quality of the machine fluid 12 remotely or from a work station. To facilitate readout, the detector 128 or the reader 132 may process the raw data to provide an alert signal 134 indicating that the machine fluid 12 needs to be replaced when the presence of the tracer 124 is detected, or when the magnitude of the characteristic signal 126 surpasses a predefined threshold.

Figure 9:
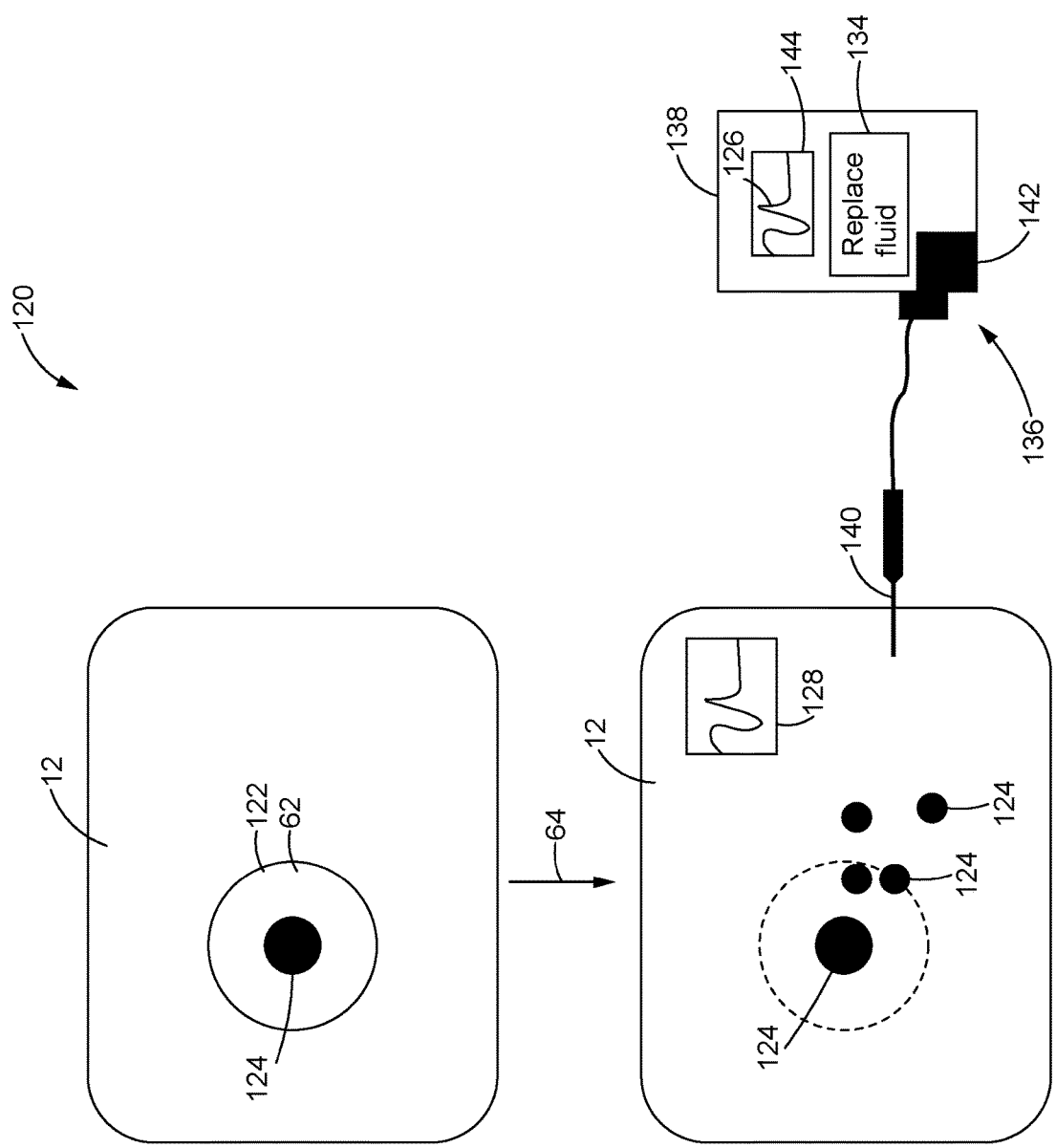
FIG. 9 is a schematic representation similar to FIG. 8, but with the release of the tracer from the capsule being monitored with a hand-held device, constructed in accordance with the present disclosure.

In another arrangement, the release of the tracer 124 into the machine fluid 12 may be monitored using a hand-held device 136 as shown in FIG. 9. The hand-held device 136 may be separate from the machine 10 and may include a reader portion 138 and a probe 140 that may be inserted into the machine fluid 12 at various locations of the fluid circuit 36 (e.g., the reservoir 40, the filter 42, the conduits 44, 48, 50, etc.). The hand-held device 136 may monitor the presence of the tracer 124 in the machine fluid 12 using a detector 142 (e.g., a UV/vis detector, a fluorescence detector, an IR detector, a light scattering detector, a viscometer or rheometer, a current or voltage detector, etc.) that may be part of the reader portion 138 or the probe 140. The detector 142 may measure the characteristic signal 126 as the probe 140 makes contact with the machine fluid 12 or draws a sample of the machine fluid 12. Raw or processed data collected by the detector 142 may be displayed at a user interface 144, enabling an operator or technician to track the quality of the machine fluid 12. In some arrangements, the hand-held device 136 may process the data to produce the alert signal 134 to notify the operator or technician that the machine fluid 12 needs to be replaced when the tracer 124 is detected or when the magnitude of the signal 126 surpasses a predefined threshold.

Figure 10:
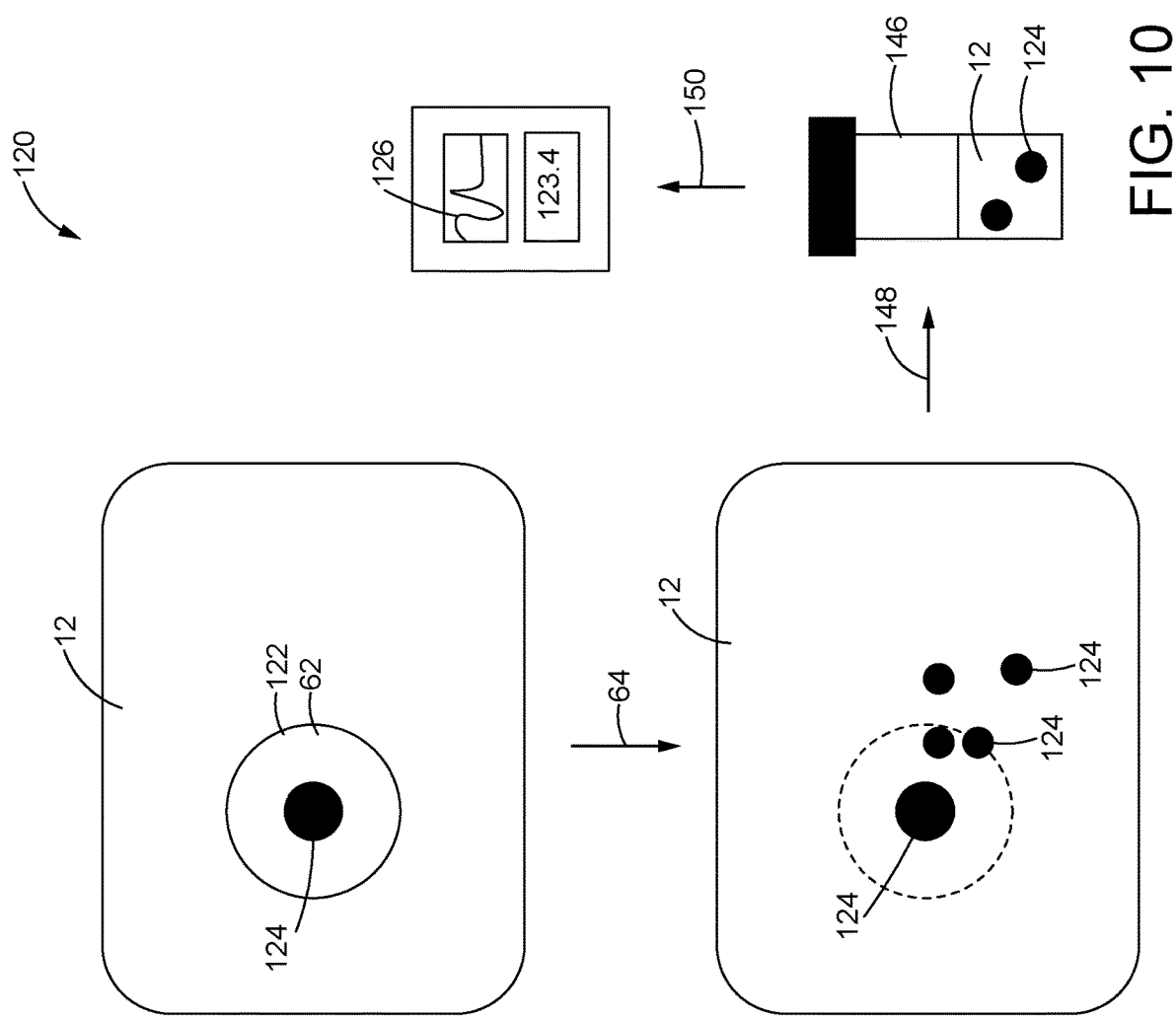
FIG. 10 is a schematic representation similar to FIG. 8, but with the release of the tracer being monitored by removing a sample of the machine fluid and analyzing the sample, constructed in accordance with the present disclosure.

FIG. 10 depicts another strategy for monitoring the release of the tracer 124 into machine fluid 12. In this arrangement, samples 146 of the machine fluid 12 may be removed 148 from the fluid circuit 36 at random or periodically during the lifetime of the machine fluid 12, and the samples 146 may be subsequently analyzed 150 for the presence of the tracer 124. Specifically, the analysis 150 of the samples 146 may involve measurements of the characteristic signal 126 using techniques apparent to those with ordinary skill in the art such as, but not limited to, UV/vis spectroscopy, fluorescence spectroscopy, atomic absorption spectroscopy, atomic emission spectroscopy, light scattering spectroscopy, FT-IR spectroscopy, current or voltage measurements, imaging techniques, viscosity or rheology measurements, visual inspection, or combinations thereof. Alternatively, or in combination with this, the analysis 150 may be carried out using one or more chemical identification techniques apparent to those with ordinary skill in the art such as, but not limited to, liquid chromatography (e.g., high-performance liquid chromatography (HPLC), thin-layer chromatography (TLC), etc.), gas chromatography, NMR spectroscopy, and mass spectrometry. As one non-limiting example, the analysis 150 may be carried out using scheduled oil sampling (S•O•S$^{SM}$) or other equivalent tests, wherein the sample 146 of the machine fluid 12 is analyzed for metals or other compounds or elements using techniques such as FT-IR and viscosity measurements. For example, if the tracer 124 is a metal, S•O•S$^{SM}$ may effectively identify the presence of trace amounts of the metal in the fluid 12. Other types of oil analysis measurements, that include oil acidity measurements, may also be used.

Figure 11:
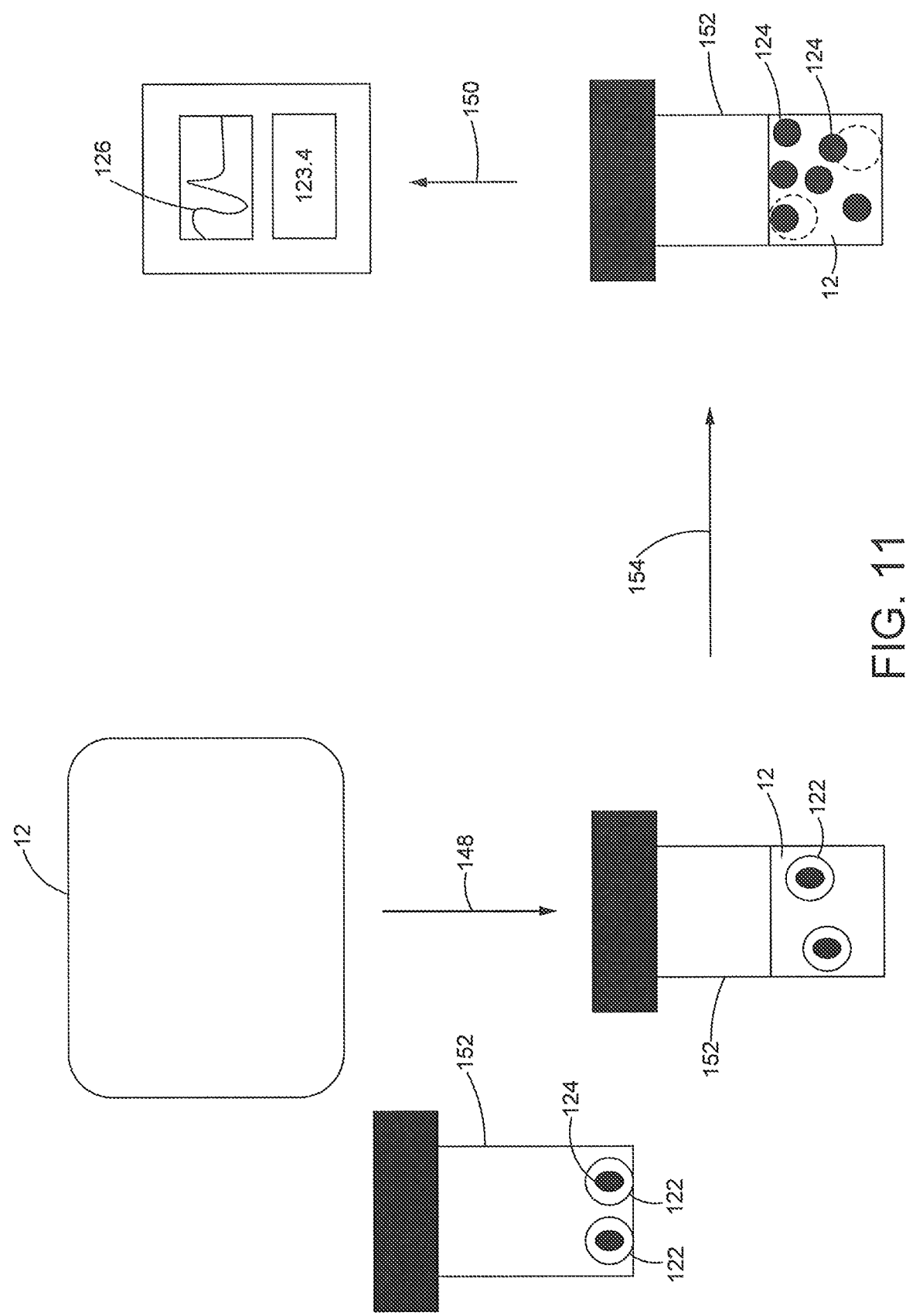
FIG. 11 is a schematic representation similar to FIG. 10, but with the release of the tracer being monitored by mixing the machine fluid with the capsule in a test container and analyzing the sample, constructed in accordance with the present disclosure.

In another arrangement, if the capsule 122 is not added to the fluid circuit 36, quantities of the machine fluid 12 may be removed 148 at random or periodically from the fluid circuit 36 and mixed with the capsule(s) 122 in a test container 152 (see FIG. 11). If the acid content of the machine fluid 12 is at a level indicative of degradation of the machine fluid 12, the dissolvable element 62 of the capsule 122 may dissolve 154 and release the tracer 124 into the machine fluid 12. Analysis 150 of the machine fluid 12 may then be performed using one or more of the techniques described above. It is further noted here that the release of the tracer 124 into the machine fluid 12 may also be monitored using a combination of any of the aforementioned strategies and detection methods.

Turning now to FIGS. 12-13, the capsule 122 encapsulating the tracer 124 may be placed in the housing 74 of the filter 42 to monitor the degradation of the machine fluid 12 flowing through the filter 42. In some cases, the capsule 122 may be secured to a specific location of the filter 42. For example, the capsule 122 may be placed on the dirty side of the filter 42, such as near the inlet 78 between the top end 76 and the top end cap 86 (FIG. 12), or near the bottom end 82 between the bottom end 82 and the bottom end cap 88 (FIG. 13). In other arrangements, the capsule 122 may be placed along the outer periphery 92 of the filter housing 74, or on the clean side of the filter 42 such as in the center tube 94. In any event, when the acid content of the machine fluid 12 reaches a level indicative of degradation, the dissolvable element 62 may dissolve, releasing the tracer 124 into the machine fluid 12 and signaling that the machine fluid 12 should to be replaced with fresh fluid. Release of the tracer 124 into the machine fluid 12 may be monitored using the on-machine detector 128 (FIG. 8), the hand-held device 136 (FIG. 9), and/or by removing samples of the machine fluid 12 (from the filter housing 74 or another location of the fluid circuit 36) and performing analysis 150 on the machine fluid 12 as described above (see FIG. 10). It is noted here that the filter 42 may be another type of engine oil filter, transmission fluid filter, hydraulic fluid filter, or coolant filter apparent to those with ordinary skill in the art, with the capsule 122 being placed on either the dirty side or the clean side of the filter 42.

INDUSTRIAL APPLICABILITY

In general, the teachings of the present disclosure may find broad applicability in many industries including, but not limited to, construction, mining, agriculture, and automotive industries. More specifically, the present disclosure may find applicability in any industry using machines or equipment that circulate a machine fluid subject to degradation with extended use such as, but not limited to, engine oil, transmission fluid, hydraulic fluid, coolant fluid, fuel, and industrial oils.

Figure 14:
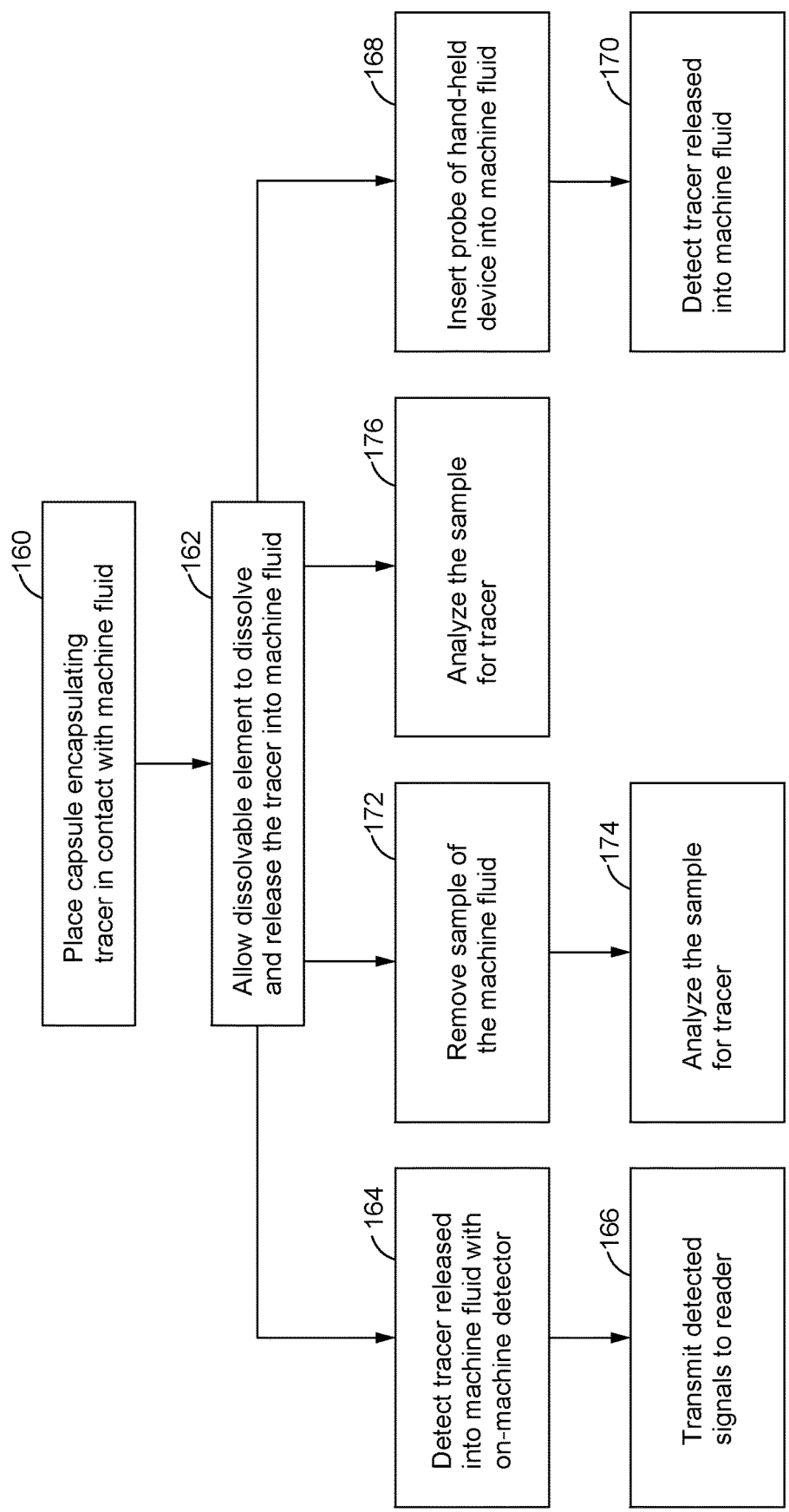
FIG. 14 is a flowchart of a series of steps involved in sensing the degradation of the machine fluid using the sensing system of FIGS. 8-13, in accordance with a method of the present disclosure.

A series of steps that may be involved in sensing the degradation of the machine fluid 12 using the sensing system 120 is shown in FIG. 14. At a block 160, the intact capsule 122 encapsulating the tracer 124 may be placed in contact with the machine fluid 12. The block 160 may involve, for example, placing a surface of the capsule 122 in contact with the machine fluid 12 or immersing the capsule 122 in the machine fluid 12 at one or more locations of the fluid circuit 36 (e.g., the filter 42, the reservoir 40, the conduits 44, 48, and 50, etc.). Alternatively, the block 160 may involve withdrawing samples of the machine fluid 12 from the fluid circuit 36 and mixing the withdrawn machine fluid samples with the capsule(s) 122 in test containers 152 (see FIG. 11). According to a next block 162, when the acid content of the machine fluid 12 reaches a level indicative of degradation, the dissolvable element 62 of the capsule 122 may be permitted to dissolve and release the tracer 124 into the machine fluid 12.

According to a block 164, the release of the tracer 124 into the machine fluid 12 may be detected with the on-machine detector 128 (also see FIG. 8). The on-machine detector 128 may transmit the detected signals (as raw or processed data) to the reader 132 (block 166), allowing an operator or technician to track the quality of the machine fluid remotely or from a work station. Alternatively, the probe 140 of the hand-held device 136 may be inserted into the machine fluid 12 at one or more locations of the fluid circuit 36 (block 168), and the release of the tracer 124 into the machine fluid 12 may be monitored using the detector 142 of the hand-held device 136 (block 170) (also see FIG. 9).

In other arrangements, samples 146 of the machine fluid 12 may be removed from the fluid circuit 36 and analyzed for the presence of the tracer 124 according to blocks 172 and 174, respectively (also see FIG. 10). If, however, the block 160 involves removing a sample of the machine fluid 12 and mixing the machine fluid 12 with the capsule 122 in a test container 152 as shown in FIG. 11, the release of the tracer 124 into the machine fluid 12 may be monitored by analyzing the machine fluid 12 in the test container 152 for the presence of the tracer 124 as described above (block 176). In any of the above arrangements, the machine fluid 12 may be replaced with fresh fluid when the release of the tracer 124 is detected, or when the detected amount of the tracer 124 in the fluid 12 (as measured by the characteristic signal 126 and/or by chemical identification techniques) reaches a predefined threshold.

The sensing system disclosed herein may provide a reliable tool for remotely tracking the quality of machine fluids that exhibit an increase in acid content with degradation. The sensing system disclosed herein may include a capsule encapsulating a tracer that may be placed in contact with the machine fluid to track the degradation of the machine fluid.

As the acid content of the machine fluid increases with use, the capsule may dissolve and release the tracer into the machine fluid, thereby notifying an operator or technician that the machine fluid should be replaced with fresh fluid. In some implementations, the capsule may be placed on the dirty side of the machine fluid filter to track the quality of the fluid prior to filtering. The sensing system disclosed herein may provide a straightforward and cost-effective strategy to monitor machine fluid degradation compared to more complex and expensive detection methods of the prior art.

It is expected that the technology disclosed herein may find wide industrial applicability in a wide range of areas such as, but not limited to, construction, automotive, marine, mining, agriculture, and earth-moving equipment applications.

What is claimed is:

1. A sensing system, comprising:
   a container configured to hold a machine fluid selected from engine oil, transmission fluid, hydraulic fluid, and coolant fluid, the machine fluid degrading when an acid content of the machine fluid reaches a level characteristic of degradation of the machine fluid;
   a filter in fluid communication with the container;
   a capsule including a dissolvable element, the dissolvable element being configured to at least partially dissolve when placed in contact with the machine fluid and when the acid content of the machine fluid reaches the level characteristic of the degradation of the machine fluid;
   a tracer encapsulated by the capsule, the tracer being at least partially released from the capsule when the dissolvable element at least partially dissolves in the machine fluid, the at least partial release of the tracer from the capsule providing a signal for the degradation of the machine fluid; and
   a detector within the container and proximate the filter, the detector detecting the signal for the degradation of the machine fluid.

2. The sensing system of claim 1, wherein the tracer produces at least one characteristic signal when released into the machine fluid.

3. The sensing system of claim 1, wherein the tracer includes a dye.

4. The sensing system of claim 1, wherein the tracer includes a fluorescent element or chromophore.

5. The sensing system of claim 1, wherein the tracer includes a compound or element having infrared (IR)-active vibrational modes.

6. The sensing system of claim 1, wherein the tracer includes a metal, a metal salt, or a metal complex.

7. The sensing system of claim 1, wherein the dissolvable element is formed from a compound selected from the group consisting of magnesium oxide, zinc oxide, cadmium oxide, and combinations thereof.

8. The sensing system of claim 1, further comprising a reader in wireless or electronic communication with the detector, the reader having a display displaying the signal.

9. A sensing system for sensing degradation of a machine fluid of a machine, comprising:
   a fluid circuit onboard the machine and having the machine fluid flowing circulating therethrough, the machine fluid being selected from engine oil, transmission fluid, coolant fluid, and hydraulic fluid;
   a filter within the fluid circuit;
   a capsule disposed within the fluid circuit and including a dissolvable element, the dissolvable element being configured to at least partially dissolve when placed in contact with the machine fluid and when an acid content of the machine fluid reaches a level characteristic of the degradation of the machine fluid; and
   a tracer encapsulated by the capsule, the tracer being at least partially released from the capsule when the dissolvable element at least partially dissolves, the at least partial release of the tracer from the capsule providing a signal for the degradation of the machine fluid; and
   a detector configured to detect the release of tracer in a location proximate the filter.

10. The sensing system of claim 9, further comprising a detector onboard the machine and within the fluid circuit, the detector detecting the signal for the degradation of the machine fluid.

11. The sensing system of claim 9, further comprising a hand-held device separate from the machine and including a probe for insertion into the machine fluid within the fluid circuit proximate the filter.

12. A sensing system for sensing degradation of a machine fluid of a machine, comprising:
   a container containing the machine fluid, the machine fluid being selected from transmission fluid, hydraulic fluid, and coolant fluid, the machine fluid degrading when an acid content of the machine fluid reaches a level characteristic of degradation of the machine fluid;
   a filter in fluid connection with the container;
   a capsule including a dissolvable element, the dissolvable element being formed from a compound selected from the group consisting of magnesium oxide, zinc oxide, cadmium oxide, and combinations thereof, the dissolvable element being configured to at least partially dissolve when placed in contact with the machine fluid and when the acid content of the machine fluid reaches the level characteristic of the degradation of the machine fluid; and
   a tracer encapsulated by the capsule, the tracer being at least partially released from the capsule when the dissolvable element at least partially dissolves in the machine fluid, the at least partial release of the tracer from the capsule providing a signal for the degradation of the machine fluid; and
   a detector configured to detect the release of tracer in a location proximate the filter.

13. The sensing system of claim 12, wherein the tracer produces at least one characteristic signal when released into the machine fluid.

14. The sensing system of claim 12, wherein the tracer includes a dye.

15. The sensing system of claim 12, wherein the tracer includes a fluorescent element or chromophore.

16. The sensing system of claim 12, wherein the tracer includes a compound or element having infrared (IR)-active vibrational modes.

17. The sensing system of claim 12, wherein the tracer includes a metal, a metal salt, or a metal complex.

18. The sensing system of claim 12, wherein the dissolvable element is formed from a compound selected from the group consisting of magnesium oxide, zinc oxide, cadmium oxide, and combinations thereof.

19. The sensing system of claim 12, further comprising a detector onboard the machine and within the fluid circuit, the detector detecting the signal for the degradation of the machine fluid.

20. The sensing system of claim 12, further comprising a hand-held device separate from the machine and including a probe for insertion into the machine fluid within the fluid circuit proximate the filter.

\* \* \* \* \*